United States Patent [19]

Mount et al.

[11] 4,425,804

[45] Jan. 17, 1984

[54] ULTRASONIC AIR FLOW TRANSDUCER FOR HIGH HUMIDITY ENVIRONMENTS

[75] Inventors: Bruce E. Mount, Diamond Bar; Con D. Rader, Villa Park, both of Calif.

[73] Assignee: The Perkin-Elmer Corp., Norwalk, Conn.

[21] Appl. No.: 316,177

[22] Filed: Oct. 29, 1981

[51] Int. Cl.³ .............................................. G01F 1/66
[52] U.S. Cl. ................................... 73/861.28; 128/725
[58] Field of Search ................... 128/725; 73/861.27, 73/861.28, 861.18, 118 A, 861.29; 248/52

[56] References Cited

U.S. PATENT DOCUMENTS

| | | | |
|---|---|---|---|
| 2,785,911 | 3/1957 | Kaufman | 248/52 |
| 3,026,868 | 3/1962 | Weinberg | 128/725 |
| 3,406,783 | 10/1968 | Haffer | 248/52 X |
| 3,575,050 | 4/1971 | Lynnworth | 73/861.27 |
| 4,114,607 | 9/1978 | Russo | 128/725 |
| 4,158,360 | 6/1979 | Adams | 128/725 |
| 4,164,865 | 8/1979 | Hall et al. | 73/861.28 |

FOREIGN PATENT DOCUMENTS 1176312  8/1964  Fed. Rep. of Germany ...... 128/725

OTHER PUBLICATIONS

Telemetry of Respiratory Air Flow, 1972, H. P. Kimmich et al., Biotelemetry Internation Symposium, 5/5–8/71, pp. 111–120.

Acoustic Gas Analyzer, ISA Transactions, vol. 17, No. 1, Charles R. Tallman, 6/78 1978, pp. 97–104.
Anesthesiology, vol. 51, No. 2, 8/79, Sukled et al., Pneumotachography: A New, Low-Dead Space, Humidity-Ind. Device.

Primary Examiner—Charles A. Ruehl
Assistant Examiner—Tom Noland
Attorney, Agent, or Firm—F. L. Masselle; T. P. Murphy; J. R. Dwyer

[57] ABSTRACT

A transducer assembly comprising an inner, primary, transducer having a pair of transducers fixed to a liner or cavity for providing the fluid compression sending and receiving signals for measuring the velocity and change of composition of fluid in the cavity which is being inspired and expired by a patient in a setting, such as in an intensive care unit of a hospital. The inner transducer is disposed in a heated housing to maintain the temperature of the inner transducer at a temperature above the saturation point of the fluid being measured and is further provided with (1) an acoustical absorber to prevent sound energy from the connection tubes, which connect the transducer assembly to endotracheal tubing, from adversely affecting fluid measurements and, (2) water absorbing material to prevent water, which might condense in the connecting tubing, from entering the inner transducer and affecting the fluid measurements.

13 Claims, 2 Drawing Figures

ULTRASONIC AIR FLOW TRANSDUCER FOR HIGH HUMIDITY ENVIRONMENTS

BACKGROUND OF THE INVENTION

This invention relates to acoustical flowmeter systems and is particularly directed to an improvement in the acoustical flowmeters of the type described and claimed in the U.S. Pat. No. 4,164,865 entitled, "Acoustical Wave Flowmeter" by L. G. Hall and R. S. Loveland, which issued Aug. 21, 1979 and the flowmeter of the U.S. Pat. No. 4,003,252 entitled, "Acoustical Wave Flowmeter" by E. J. DeWath, which issued Jan. 18, 1977.

The transducer of the Hall and Loveland system eliminated all impediments to the flow path of the fluid, all cavities in which debris might collect, measured flow accurately regardless of changes in fluid composition or temperature, and determined a change in velocity of sound of the fluid being measured as a function of fluid density. The advantages of the Hall and Loveland system, and manner in which the system functions, is clearly set forth in the Hall and Loveland patent, supra.

Since this is a very highly accurate fluid flow measuring system, one of the many applications is to determine the velocity of fluid or gases (volume flow rate) inspired and expired by a hospitalized patient suffering from lung disease or recent chest surgery. However, such an environment is hostile to the proper operation of the system because of the temperature at which the room, an intensive care unit (ICU) for example, is maintained. The air delivered to the patient's lung is 100% saturated and the room where the system is located is at a temperature which normally causes water to condense out of the delivered and expired air. As a consequence, an accurate determination of volume flow rate cannot be made if water droplets form on the inside of the transducer, or if water condenses in the connecting tubing and is allowed to run through the transducer.

This invention overcomes the problem of operating in such an environment and enables an accurate determination of the volume flow rate inspired and expired by the hospitalized patient and adapted to be connected to standard air delivery tubing as used in hospital intensive care units.

SUMMARY OF THE INVENTION

The transducer assembly of this invention comprises a primary transducer having a pair of transducers fixed to an inner liner or tubing for providing the compression sending and receiving signals for measuring the velocity and change of composition of the fluid in the liner being inspired and expired by a patient. The transducer tubing is in a housing which is heated to maintain the temperature of the transducer tubing at a temperature above the saturation point of the fluid being measured and is further provided with (1) an acoustical absorber to prevent sound energy from connecting tubes (connecting the transducer assembly to the patient) to adversely affect flow measurement and, (2) water absorbing material to prevent water which might condense in the connecting tubing from entering the transducer tubing and affecting flow measurements.

DETAILED DESCRIPTION

Figure 1:
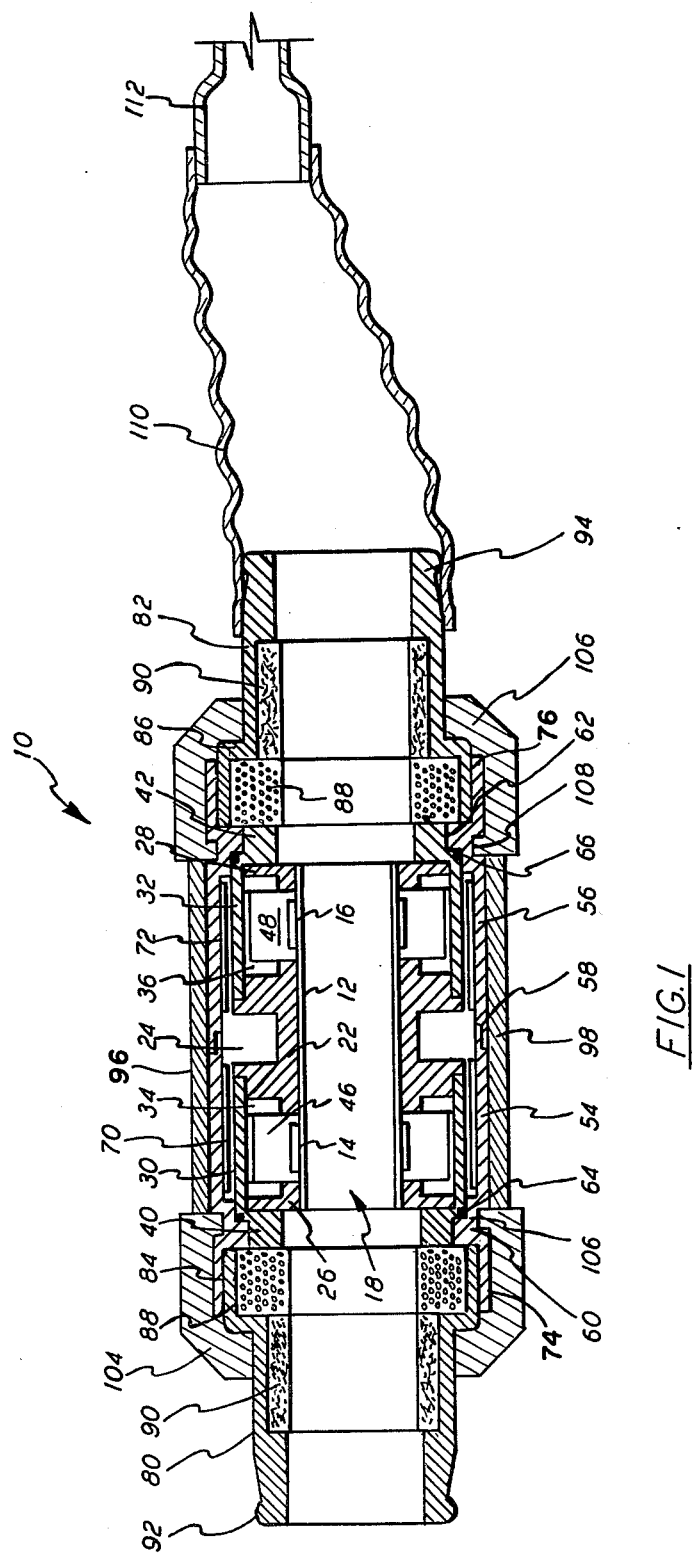
FIG. 1 is an elevational view, in cross-section, of the transducer assembly constructed in accordance with the teachings of this invention and shown connected to standard air delivery tubing such as used in hospital intensive care units.
Figure 2:
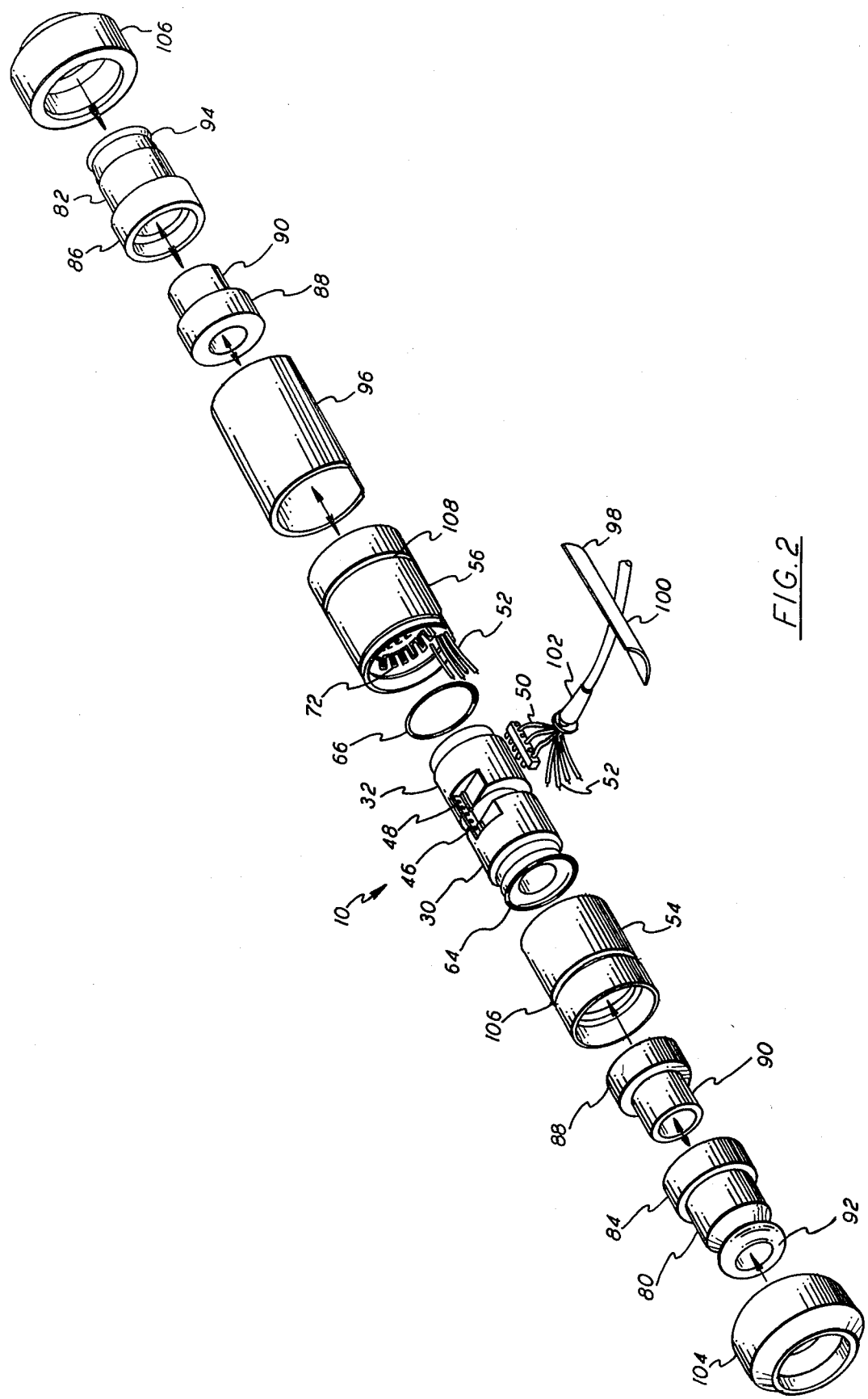
FIG. 2 is an exploded view of the various components of the transducer assembly of FIG. 1.

FIGS. 1 and 2 disclose a flow transducer assembly 10 to measure the volume flow rate of inspired and expired gases by a hospitalized patient. The assembly includes a relatively thin tube, or liner 12, having a pair of signal transducers (sometimes called "active elements") 14 and 16 spaced apart along the length of the tube. This liner and the transducers comprise the primary flow measuring means, or inner transducer, identified as 18, and produces the ultrasonic acoustic compressions at selected frequencies in the fluid within the tubing. These active elements 14 and 16 are alternately switched into a transmit and receive mode to generate upstream and downstream transmitted and received signals. The operation of the transducers 14 and 16 on the fluid and the means of processing the information derived by these transducers are fully disclosed in the Hall and Loveland patent, supra, to which reference is made. One form of the transducers and a method of making them are disclosed and claimed in another patent application by one of the co-inventors in this application. This application is entitled, "Method for Electrical Connection to Thin Film Coatings, and the Electrical Connector Formed Thereby", Ser. No. 316,176, filed Oct. 29, 1981.

The inner or primary transducer 18 is positioned in a multi-piece shell comprising a double walled ring 22, U shaped in cross-section, which defines a cavity 24 therebetween, a pair of outer spacer rings 26 and 28 and two bell shaped cover members 30 and 32 which engage the spacer rings and double walled ring 22 to define a pair of cavities 34 and 36. The double walled ring 22 and spacer rings 26 and 28 have central apertures of the same diameter as the outside diameter of the liner 12 to support the liner. The double walled ring may be made of two halves or fitted on the liner before one of the transducers is formed thereon. The bell shaped cover members each have inwardly directed integral rings 40 and 42 to engage and position the spacer rings 26 and 28. These spacer rings, 26 and 28 also position the transducer 14 and 16 within the cavities 34 and 36. The means for connecting the transducers with a source of high frequency energy are illustrated only schematically at 46 and 48 and are enclosed in cavities 34 and 36 together with part of the wiring 50. Again, for the details of the means for connecting the transducers to a source of energy, reference is again made to the patent application supra. The details of the connections are not described fully herein since such detail is unnecessary to the understanding of this invention. The central cavity 24 accommodates additional wiring 52. The above described shell pieces and retainer rings are of a suitable plastic material, such as Kynar material available from Pennwalt Company of King of Prussia, Pa.

The multi-piece shell is, in turn, encased in a tubular housing comprising two bell shaped halves 54 and 56 of suitable metal, such as aluminum, which, together, are longer than the shell and liner and are sealed, as by epoxy, at their overlapping edges 58. The halves of the housing are provided with inwardly directed integral rings 60 and 62 which engage the outer periphery of rings 40 and 42 of the shell. O-ring seals 64 and 66, located between the rings of the shell and the rings of the housing, seal the housing against any leakage of fluid from the flow path through the transducer assembly. The inner walls of the housing which encase the shell, being of a larger radius, are spaced from the outer walls of the bell shaped cover members 30 and 32 of the shell and provided with heating elements 70 and 72, plated and etched, in a conventional manner and connected to wiring 52 within the central cavity 24. The wiring 52 is, of course, connectable to a voltage source for activating the heating elements. The open ends 74 and 76 of the housing facing outwardly from the shell are of a large inner diameter than rings 40 and 42 are formed to receive a pair of removable bell shaped end fittings 80 and 82. These end fittings are of suitable metal, such as aluminum, and have ends 84 and 86 with the largest radius which fit snugly into the open ends 74 and 76 and are further provided with water absorbing material 88 and acoustic energy absorbing material 90. The acoustic energy absorbing material, as mentioned previously, is to prevent sound energy from the connecting tubes to which the transducer assembly is connected from adversely affecting fluid measurements. The water absorbing material is in the form of a ring located in the large radius portions 84 and 86 so as to engage the rings of the shell and housing and thus are located closer to the inner transducer than the acoustic energy absorbing material. The water absorbing material is also in the form of a ring and is thus located between the acoustic energy absorbing material and the open lipped edges 92 and 94 of the end fittings. Both the acoustic energy absorbing ring and the water absorbing ring, being centrally apertured, form part of the flow path of the fluid through the transducer assembly and are, respectively, of polyurethane form (90) and cellulose sponge (88). The two rings may be encased in a cover (not shown) which makes them easily replaceable as a unit in the end fittings as shown in FIG. 2.

Finally, to complete the assembly, the housing is encircled with a two piece insulator cover 96 and 98 of suitable plastic material, such as acrylic and which, being open longitudinally, snaps over the housing (see FIG. 2). Cover piece 98 is provided with an aperture 100 to receive a cable flexure 102 to prevent cable breakage. The cable flexure and cover piece 98 are provided with a sealant to seal the (wire) entrance against moisture. To hold the end fittings onto the housing removable caps 104 and 106 of suitable plastic material, such as silicone rubber, are fitted over the large radius portion 84 and 86 of the end fittings and, being resilient, snap into radial grooves 107 and 108 in the housing.

In operation, the lip portions of the end fittings engage flexible tubing 110, a standard in the industry, and is, in turn, connected to an endotracheal tubing 112 for connection to a patient's throat to enable positive-pressure inflation of the patient's lungs.

In normal use, the transducer assembly 10 is placed at a lower level than the endotracheal tube and inclined away from the tube to prevent condensed water from entering the patient's lungs. The water absorption rings 86 and 88 absorb water which condenses in the flexible tubing 110 and passes through the acoustic rings 90 and 92. Otherwise, the water would eventually run into the inner transducer and disturb the flow measurement readings. The housing is heated to a temperature of approximately 40° C. by the heater elements 70 and 72 which is higher than the saturated air temperature delivered to the patient (typically 30° C. to 35° C.) The housing being thermally conductive, heats the thermally conductive end fittings so that their temperature will remain essentially the same as that of the housing. The heating of the housing also maintains the water absorbing material at an elevated temperature to increase its absorption characteristics. Too, the caps 104 and 106 and outer covering 96 and 98, being of low thermal conductivity material, reduce heat loss from the housing and end fittings.

What is claimed is:

1. In a transducer assembly for measuring the volume flow rate of gaseous fluids along a path and useable particularly in high humidity environments and which includes an inner transducer having means defining a substantially cylindrical cavity and a pair of substantially cylindrical signal transducers disposed along said cavity and responsive to alternately produced signals applied to each of the pair of signal transducers to produce acoustic compressions in the fluid during the transmit signal from one signal transducer and to produce received signals responsive to said acoustic compression in the other signal transducer which signals are proportional to the velocity of the acoustic compressions traveling from the first to the second signal transducer, the improvement comprising, means for heating the inner transducer to maintain the fluid in said cavity at a temperature higher than ambient temperature to maintain the fluid in the cavity below saturation point to prevent moisture from forming in said cavity.

2. The transducer assembly as claimed in claim 1 further including acoustic absorbing means for preventing acoustic compression energy from leaving said inner transducer so that such energy will not enter any external tubing system to which the transducer assembly may be connected, which energy would otherwise randomly be reflected back into the cavity and adversely affect flow measurement.

3. The transducer assembly as claimed in claim 2 further including means for absorbing moisture which may condense in the tubing to which the transducer assembly is connected and which would otherwise flow into the cavity.

4. The transducer assembly as claimed in claim 2 wherein said inner transducer is disposed in a housing, said housing having heating elements therein which form said heating means.

5. The transducer assembly as claimed in claim 4 wherein moisture absorbing means are located at each end of said cavity.

6. The transducer assembly as claimed in claim 5 wherein said energy absorbing means are located adjacent to said moisture absorbing means.

7. The transducer assembly as claimed in claim 6 wherein said housing is heat conductive along a substantial portion of the length of the transducer assembly to conduct heat from the heating elements throughout the transducer assembly to maintain the entire transducer assembly at a uniform temperature.

8. The transducer assembly as claimed in claim 7 further including end fittings on each end of the housing to enable connection of the transducer assembly to standard delivery tubing such as used in hospital intensive care units for positive-pressure ventilation of patients.

9. The transducer assembly as claimed in claim 8 wherein said moisture absorbing means and said energy absorbing means are located in said end fittings.

10. The transducer assembly as claimed in claim 9 further including means for encasing said housing and portions of said end fittings in insulation means to aid in maintaining the temperature of the transducer assembly at a uniform temperature.

11. The transducer assembly as claimed in claim 10 wherein said insulation means includes two cap members, said cap members engaging portions of said end fittings and portions of said housing to removably secure said end fittings to said housing.

12. The transducer assembly as claimed in claim 11 wherein said energy absorbing means are substantially cylindrical.

13. The transducer assembly as claimed in claim 12 wherein said moisture absorbing means are substantially cylindrical.

* * * * *